(12) United States Patent
Vorwaller et al.

(10) Patent No.: US 11,865,356 B1
(45) Date of Patent: Jan. 9, 2024

(54) LIGHT THERAPY DEVICE

(71) Applicant: Theralight, LLC, Lindon, UT (US)

(72) Inventors: Charles Vorwaller, Parker, CO (US); Justin Vorwaller, Provo, UT (US); Lin Yang, Wuhan (CN); Brian H. Probst, Provo, UT (US)

(73) Assignee: Theralight, LLC, Lindon, UT (US)

( * ) Notice: Subject to any disclaimer, the term of this patent is extended or adjusted under 35 U.S.C. 154(b) by 0 days.

(21) Appl. No.: 17/465,656

(22) Filed: Sep. 2, 2021

Related U.S. Application Data

(63) Continuation of application No. 16/840,273, filed on Apr. 3, 2020, now abandoned.

(60) Provisional application No. 62/828,747, filed on Apr. 3, 2019, provisional application No. 62/828,816, filed on Apr. 3, 2019.

(51) Int. Cl.
*A61N 5/06* (2006.01)
*A61N 5/067* (2006.01)

(52) U.S. Cl.
CPC ............... *A61N 5/06* (2013.01); *A61N 5/067* (2021.08); *A61N 2005/064* (2013.01); *A61N 2005/0626* (2013.01); *A61N 2005/0637* (2013.01); *A61N 2005/0642* (2013.01); *A61N 2005/0651* (2013.01); *A61N 2005/0654* (2013.01)

(58) Field of Classification Search
CPC .. A61N 5/06; A61N 5/067; A61N 2005/0626; A61N 2005/0637; A61N 2005/064; A61N 2005/0642; A61N 2005/0651; A61N 2005/0654
See application file for complete search history.

(56) References Cited

U.S. PATENT DOCUMENTS

2011/0071602 A1* 3/2011 Irge ................ A61N 5/0613
607/88
2015/0025601 A1* 1/2015 Fiset ............... A61N 5/0617
607/94
2019/0083809 A1* 3/2019 Zhang ............. A61N 5/0616

FOREIGN PATENT DOCUMENTS

EP          3246069 A1 * 11/2017  ........... A61N 5/0613

* cited by examiner

*Primary Examiner* — Carl H Layno
*Assistant Examiner* — Aya Ziad Bakkar
(74) *Attorney, Agent, or Firm* — Thorpe North & Western, LLP; David W. Osborne (57) ABSTRACT

Technology for a light therapy device is disclosed. The light therapy device can comprise: a housing; and a combination of light sources coupled to the housing in an orientation operable to radiate a subject, and provide light therapy from the combination of light sources. The combination of light sources can include: a first discrete light source configured to emit light at a wavelength limited to between about 500 nanometers (nm) to about 700 nm; a second discrete light source configured to emit light at a wavelength limited to between about 700 nm to about 850 nm; a third discrete light source configured to emit light at a wavelength limited to between about 800 nm to about 900 nm; and a fourth discrete light source configured to emit light at a wavelength limited to between about 850 nm to about 1050 nm.

21 Claims, 10 Drawing Sheets

LED CHAMBER SPECIFICATION

Power Input:
1. The input to the chamber will allow for either:
   - One-Phase 220v 30A power cable.

2. The power supply should be modular and rack mounted. If the system has a power supply failure, we want to be able to send them a replacement part and not a technician.

LED Output
Pulsing Output:

1. The system shall have programmable pulsing of the LED array. The pulse rate should be programmable in the range from 10 Hz to 5000Hz. If possible with the default being about 40Hz or 10Hz for most applications.

2. The pulsing of the system will be at an 85% duty cycle.

3. Wavelength: 633nm, 810nm, 850nm, 940nm

|     | Wavelength | Number of Diode | Power Consumption (W) |
| --- | --- | --- | --- |
| Red | 633nm | 11520 | 896 |
| IR  | 810nm | 5760  | 448 |
| IR  | 850nm | 21960 | 1708 |
| IR  | 940nm | 11520 | 896 |
|     |       | 45000 | 3500 |

633:810:850:940= 2: 1: 4: 1= 32pcs: 16pcs: 61pcs : 16pcs
Total: 125pcs LED Bars

SIZE:
2440mm*1180mm*1370mm

Power Density: Max. 80mW/cm$^2$

FIG. 3A

FAT LOSS SPECTRUM

|  | Wavelength | Number of Diodes | Power Consumption (W) |
|---|---|---|---|
| RED | 633nm | 23040 | 1792 |
| IR | 850nm | 11160 | 868 |
| IR | 940nm | 10800 | 840 |
|  | Total | 45000 | 3500 |

LED CHAMBER SPECIFICATION

Power Input:

1. Input to the chamber allows for a one-Phase 220v 30A power cable.
2. Power supply is modular and rack mounted. If the system has a power supply failure, replacement part can be provided.

LED Output CW to Pulsing Output:

1. The system is programmable pulsing of the LED array. The pulse rate is programmable in the range from CW to 5000Hz.
2. The pulsing of the system is at an 85% duty cycle.
3. Wavelength: 633nm, 850nm, 940nm.

633:850:940 = 2:1:1 = 64pcs: 31pcs: 30pcs
Total: 125 pieces LED Bars

SIZE: 2440mm*1180mm*1370mm

Power Density: Max. 80mW/cm²

LIGHT THERAPY DEVICE

RELATED APPLICATIONS

This application is a continuation of U.S. patent application Ser. No. 16/840,273, filed Apr. 3, 2020, which claims priority to U.S. Provisional Patent Application No. 62/828,816, filed Apr. 3, 2019 and U.S. Provisional Patent Application No. 62/828,747, filed Apr. 3, 2019, which are incorporated herein by reference.

BACKGROUND

As cells age and undergo stress, mitochondria can produce Nitric oxide (NO) which competes with and interferes with oxygen. Nitric oxide can occupy the receptor site that oxygen binds during respiration, in which sugar is transformed into cellular energy. A diet high in anti-oxidants can mitigate the amount of excess NO. However, cells do not always properly remove the excess NO, which can cause ROS (reactive oxygen species) and oxidative stress. Reactive oxygen species can result in inflammation, cell death, and the expression of genes responsible for cancer, Alzheimer's, osteoarthritis, and other diseases.

Photo-bio-modulation therapy (PBMT), also known as LLLT (low level laser therapy), involves exposing the body to certain light wavelengths to stimulate healing and reduce inflammation and pain. Phototherapy can be delivered at a doctor's office or at home using various devices.

BRIEF DESCRIPTION OF THE DRAWINGS

Features and advantages of technology embodiments will be apparent from the detailed description which follows, taken in conjunction with the accompanying drawings, which together illustrate, by way of example, various technology features; and, wherein.

Reference will now be made to the exemplary embodiments illustrated, and specific language will be used herein to describe the same. It will nevertheless be understood that no limitation on technology scope is thereby intended.

DESCRIPTION OF EMBODIMENTS

Before the disclosed technology embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting. The same reference numerals in different drawings represent the same element. Numbers provided in flow charts and processes are provided for clarity in illustrating steps and operations and do not necessarily indicate a particular order or sequence.

Definitions

As used in this written description, the singular forms "a," "an" and "the" include express support for plural referents unless the context clearly dictates otherwise. Thus, for example, reference to "a light source" includes a plurality of such light sources.

Reference throughout this specification to "an example" means that a particular feature, structure, or characteristic described in connection with the example is included in at least one embodiment of the present invention. Thus, appearances of the phrases "in an example" or "an embodiment" in various places throughout this specification are not necessarily all referring to the same embodiment.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present technology can be referred to herein along with alternatives for the various components thereof. It is understood that such embodiments, examples, and alternatives are not to be construed as de facto equivalents of one another, but are to be considered as separate and autonomous representations under the present disclosure.

Furthermore, the described features, structures, or characteristics can be combined in any suitable manner in one or more embodiments. In the following description, numerous specific details are provided, such as examples of layouts, distances, network examples, etc., to provide a thorough understanding of invention embodiments. One skilled in the relevant art will recognize, however, that the technology can be practiced without one or more of the specific details, or with other methods, components, layouts, etc. In other instances, well-known structures, materials, or operations may not be shown or described in detail to avoid obscuring aspects of the disclosure.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "coupled" and "connected" can be used interchangeably and refer to a relationship between items or structures that are either directly or indirectly connected in an electrical or nonelectrical manner. "Directly coupled" or "directly connected" objects or elements are in physical contact with one another. In this written description, recitation of "coupled" or "connected" provides express support for "directly coupled" or "directly connected" and vice versa. Objects described herein as being "adjacent to" each other may be in physical contact with each other, in close proximity to each other, or in the same general region or area as each other, as appropriate for the context in which the phrase is used.

Occurrences of the phrase "in one embodiment," or "in one aspect," herein do not necessarily all refer to the same embodiment or aspect.

As used herein, comparative terms such as "increased," "decreased," "better," "worse," "higher," "lower," "enhanced," "maximized," "minimized," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, an "increased" healing response can refer to a degree or timing of healing that surpasses or exceed healing achieved to a comparable injury or condition without treatment or without a similar or like treatment. Likewise, an "increased" recovery can refer to a degree or timing of recovery that surpasses or exceeds a recover achieved in the absence of treatment, or a similar or like treatment.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, "effective" or "therapeutically effective" when used in connection with a treatment, such as a light therapy treatment, refer to an amount and/or type of treatment components that is determined to be sufficient to achieve therapeutic results in treating a subject for a given condition. It is understood that various biological factors may affect the ability of a treatment or therapy to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of medical sciences.

As used herein, a "therapeutically effective combination" is a combination of lights or light sources that are applied in an amount (e.g. intensity or duration or both) that is sufficient to provide a beneficial effect to a subject irradiated with the light therapy.

The terms "patient," "subject" and "individual" are interchangeably used to mean a warm-blooded animal, such as a mammal, suffering from a disease, condition, or disorder. It is understood that humans and animals are included within the scope of the term "subject," "subject" or "individual."

A "disease" is a state of health of a subject wherein the subject cannot maintain homeostasis, and wherein if the disease is not ameliorated then the subject's health continues to deteriorate. A "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. An "injury" refers to trauma or damage imposed by an event or by a disease or disorder. For example, over-exertion can cause muscular damage in a subject. A "condition" can be used to refer to diseases, disorders, or injuries and includes both physical and mental conditions and the manifest symptoms thereof. A condition, including diseases, disorders, and injuries as well as symptoms thereof is "alleviated" if the severity of a symptom of the condition, the frequency with which such a symptom is experienced by a patient, or both, is reduced.

The terms "treat," "treatment," "treating" and the like as used herein, refer to the alleviation (i.e., "diminution") and/or the elimination of a sign or symptom or a source of a sign or symptom of a disease, condition, or disorder. By way of several non-limiting examples, a symptom of a bacterial infection can be treated by alleviating a symptom of that disorder. A symptom of a bacterial infection can also be treated by altogether eliminating a symptom of that disorder. A bacterial infection or colonization can be treated by alleviating the source, or "cause," of that disorder. A bacterial infection or colonization can also be treated by eliminating the source of that disorder. Additionally, inflammation is a condition that can be associated with a number of diseases or injuries. Administration of anti-inflammatory agents, such as ibuprofen or acetaminophen can reduce inflammation and thereby provide an effective treatment.

Numerical amounts and data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

Description

An initial overview of technology embodiments is provided below and then specific technology embodiments are described in further detail later. This initial summary is intended to aid readers in understanding the technology more quickly, but is not intended to identify key or essential technological features nor is it intended to limit the scope of the claimed subject matter. Unless defined otherwise, all technical and scientific terms used herein have the same meaning as commonly understood by one of ordinary skill in the art to which this disclosure belongs.

As cells age and undergo stress, mitochondria can produce nitric oxide (NO) which competes with and interferes with oxygen. When cells do not properly remove the excess NO, an increase in the amount of reactive oxygen species (ROS) can occur. Reactive oxygen species can result in inflammation, cell death, and the expression of genes responsible for cancer, Alzheimer's, osteoarthritis, and other diseases.

Photo-bio-modulation therapy (PBMT), also known as low level laser therapy (LLLT), involves exposing the body to certain light wavelengths to stimulate healing and reduce inflammation and pain. However, light therapy has previously been based on light emitters without an adequate variance in wavelength. For example, a light therapy product including only one wavelength of light emitting elements would be impracticable to modify for operation with a wide range of subjects without the assistance of a trained technician to replace the light emitting elements at a high cost. Because each subject may be responsive to a different combination of light therapy parameters (e.g., light wavelength, pulse/continuous wave, combination of light wavelengths, power level, and the like), it can become uneconomical to adequately treat subjects with different responses to light therapy.

Previous light therapy approaches have involved an inadequate amount of power. Achieving deep photon penetration is desirable in treatment with light-based therapies. The use of visible light (e.g., 380 nm to 700 nm) can be practical for skin and other directly accessible tissues but not for deeper tissues because of strong absorption by blood and scattering from tissue components. Near-infrared (NIR) light (e.g., 650 nm to 950 nm) can be used to for deeper penetration into tissues. However, the power of the near-infrared light should be adequate. Previous light therapy approaches have also used treatment beam sizes and operating modes that have not allowed for adequate penetration into deeper tissues.

The present invention provides a number of enhancements over previous light therapy devices. For example, as presented herein, a combination of light sources can by administered to a subject in order to provide a therapeutic effect. In some embodiments, it has been unexpectedly found that a combination of certain light emitting elements or sources with a particular power and wavelength can provide a synergistic effect in enhancing well-being and healing when treating a range of subjects. It is well understood that a synergistic effect occurs when a result achieved is more than the merely additive effect provided by a combination of elements. When red light and near-infrared light is absorbed by the mitochondria protein Cytochrome c Oxidase (CcO), mitochondrial NO can dissociate from CcO and enhance oxygen transport. CcO is one of the final enzymes in the respiratory electron transport chain; therefore, increased functioning of CcO can increase ATP production. A subsequent decrease in reactive oxygen species can decrease inflammation, cell death, and the like.

The present invention relates to devices, systems, and methods comprising a light therapy device including a housing and a synergistic combination of light sources coupled to the housing in an orientation operable to radiate a subject. The light therapy from the combination of light sources can include one or more of: a first discrete light source configured to emit light at a wavelength limited to between about 500 nanometers (nm) to about 700 nm; a second discrete light source configured to emit light at a wavelength limited to between about 700 nm to about 850 nm; a third discrete light source configured to emit light at a wavelength limited to between about 800 nm to about 900 nm; and a fourth discrete light source configured to emit light at a wavelength limited to between about 850 nm to about 1050 nm.

In one aspect, the present invention provides devices, systems, and methods useful for the treatment of diseases and disorders. In one embodiment, the devices, systems, and methods of the present invention are useful for the treatment of pain (e.g., muscle pain or joint pain), stiffness, inflammation, arthritis, obesity, or combinations thereof in a subject. In one embodiment, the present invention provides devices, systems, and methods useful for the stimulation of blood circulation, lactic acid clearance, tissue regeneration, muscle or joint mobility, muscle regeneration, weight loss, or combinations thereof in a subject. It should be appreciated that the devices, systems, and methods of the present invention may be suitable for treating any infection caused by a microorganism or pathogen, including a bacterium, a virus, a fungus, a protozoan, a parasite, an arthropod, and the like.

In one aspect, the present invention provides a light therapy system comprising a light therapy device and a controller configured to select a parameter of emission by the light sources. The controller can be configured to adjust one or more of a pulse rate of the combination of light sources, a combined power density of the combination of light sources, a combined power of the combination of light sources, a timer to activate or deactivate the power of the light therapy device; a combined power density of the combination of light sources over a selected period of time; or a combined power of the combination of light sources over a selected period of time; or an output of one or more speakers. The light therapy system can further comprise a graphical user interface.

Figure 1:
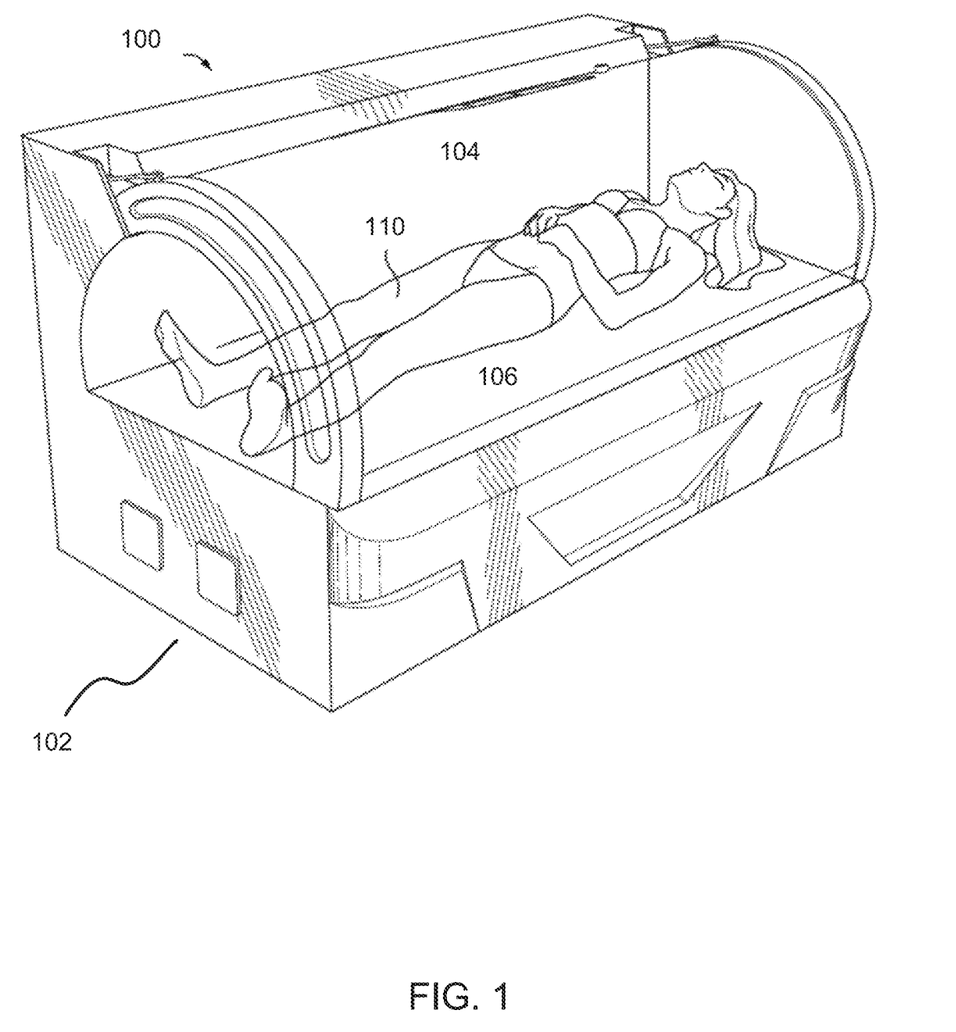
FIG. 1 illustrates a light therapy chamber in accordance with an example.

In one example, as illustrated in FIG. 1, a light therapy device 100 can comprise a housing 102 and a combination of light sources 104, 106 coupled to the housing 102. The combination of light sources 104, 106 can be in an orientation operable to radiate a subject 110. The combination of light sources 104, 106 can provide light therapy to the subject 110 in this manner.

In one example, the combination of light sources can include: (a) a first discrete light source configured to emit light at a wavelength limited to between about 500 nanometers (nm) to about 700 nm, (b) a second discrete light source configured to emit light at a wavelength limited to between about 700 nm to about 850 nm, (c) a third discrete light source configured to emit light at a wavelength limited to between about 800 nm to about 900 nm, and (d) a fourth discrete light source configured to emit light at a wavelength limited to between about 850 nm to about 1050 nm.

In another example, the first discrete light source configured to emit light at a wavelength can be limited to be between about 500 nm to about 700 nm, which includes light in the visible light spectrum. In another example, the first discrete light source can be configured to emit light at a wavelength limited to between about 580 nm and 680 nm. In another example, the first discrete light source can be configured to emit light at a wavelength limited to between about 600 nm and 665 nm. In another example, the first discrete light source can be configured to emit light at a wavelength limited to between about 620 nm and 645 nm. In another example, the plurality of first discrete light sources can be limited to be between about 20% to about 30% of the combination of light sources. In another example, the plurality of first discrete light sources can be limited to be between about 10% to about 40% of the combination of light sources.

In another example, the second discrete light source configured to emit light at a wavelength can be limited to be between about 700 nm to about 850 nm, which includes light in the near-infrared (NIR) light spectrum. In another example, the second discrete light source can be configured to emit light at a wavelength limited to between about 750 nm and 830 nm. In another example, the second discrete light source can be configured to emit light at a wavelength limited to between about 770 nm and 830 nm. In another example, the second discrete light source can be configured to emit light at a wavelength limited to between about 800 nm and 820 nm. In another example, the plurality of second discrete light sources can be limited to be between about 8% to about 16% of the combination of light sources. In another example, the plurality of second discrete light sources can be limited to be between about 5% to about 24% of the combination of light sources.

In another example, the third discrete light source configured to emit light at a wavelength can be limited to between about 800 nm to about 900 nm, which includes light in the near-infrared (NIR) light spectrum. In another example, the third discrete light source can be configured to emit light at a wavelength limited to between about 820 nm and 880 nm. In another example, the third discrete light source can be configured to emit light at a wavelength limited to between about 830 nm and 870 nm. In another example, the third discrete light source can be configured to emit light at a wavelength limited to between about 840 nm and 860 nm. In another example, the plurality of third discrete light sources can be limited to be between about 40% to about 60% of the combination of light sources. In another example, the plurality of third discrete light sources can be limited to be between about 20% to about 80% of the combination of light sources.

In another example, the fourth discrete light source configured to emit light at a wavelength can be limited to be between about 850 nm to about 1050 nm, which includes light in the near-infrared (NIR) light spectrum. In another example, the fourth discrete light source can be configured to emit light at a wavelength limited to between about 900 nm and 1000 nm. In another example, the fourth discrete light source can be configured to emit light at a wavelength limited to between about 920 nm and 980 nm. In another example, the fourth discrete light source can be configured to emit light at a wavelength limited to between about 930 nm and 950 nm. In another example, the plurality of fourth discrete light sources can be limited to be between about 15% to about 35% of the combination of light sources. In another example, the plurality of fourth discrete light sources can be limited to be between about 5% to about 55% of the combination of light sources.

Figure 2A:
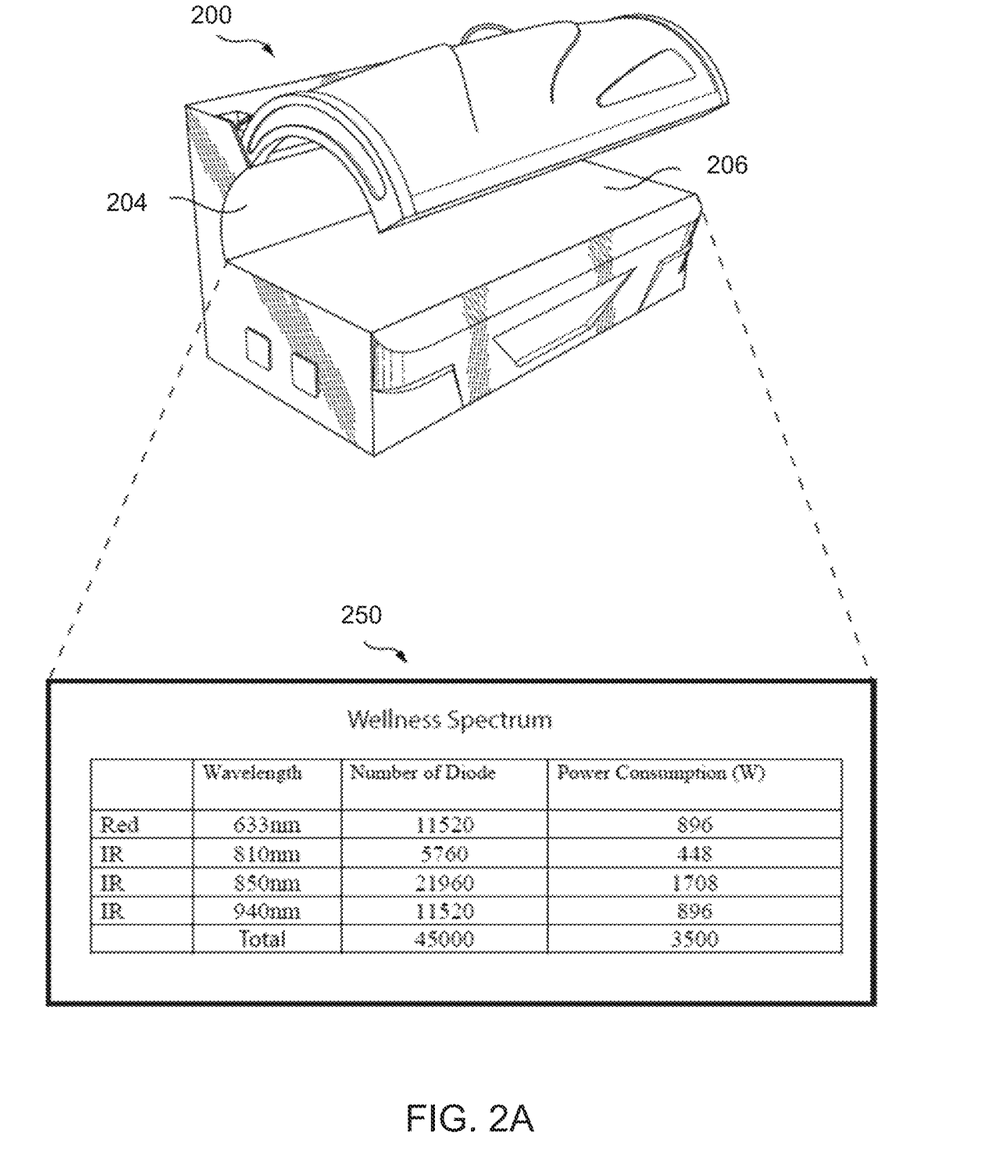
FIG. 2a illustrates a light therapy chamber with operating parameters in accordance with an example.

In another example, as illustrated in FIG. 2a, a light therapy device 200 with a combination of light sources 204, 206 can be configured with various operating parameters including: an adjustable power density, an adjustable body coverage percentage, an adjustable frequency control, an adjustable percentage of each discrete light source, an adjustable session time, an adjustable continuous wave or pulse wave, and the like. The table 250 in FIG. 2A depicts a wellness spectrum using 4 wavelengths of light.

In one example, the combination of light sources can be configured to pulse at a rate limited to between about 10 hertz (Hz) to about 5 kilohertz (kHz). In another example, a continuous wave can be used. In another example, the combination of light sources can be configured to pulse using a duty cycle limited to be between about 75% to about 100%.

In this example, (a) the first discrete light source can emit at a wavelength of about 633 nm, (b) the second discrete light source can emit at a wavelength of about 810 nm, (c) the third discrete light source can emit at a wavelength of about 850 nm, and (d) the fourth discrete light source can emit at a wavelength of about 940 nm.

In this example, (a) about 11520 first discrete light sources can emit at a wavelength of about 633 nm, (b) about 5760 second discrete light sources can emit at a wavelength of about 810 nm, (c) about 21960 third discrete light sources can emit at a wavelength of about 850 nm, and (d) about 11520 fourth discrete light sources can emit at a wavelength of about 940 nm.

In this example, the total power consumption in Watts (W) can be 3500. In this example, (a) the first discrete light sources can consume about 896 W, (b) the second discrete light sources can consume about 448 W, (c) the third discrete light sources can consume about 1708 W, and (d) the fourth discrete light sources can consume about 896 W.

Figure 2B:
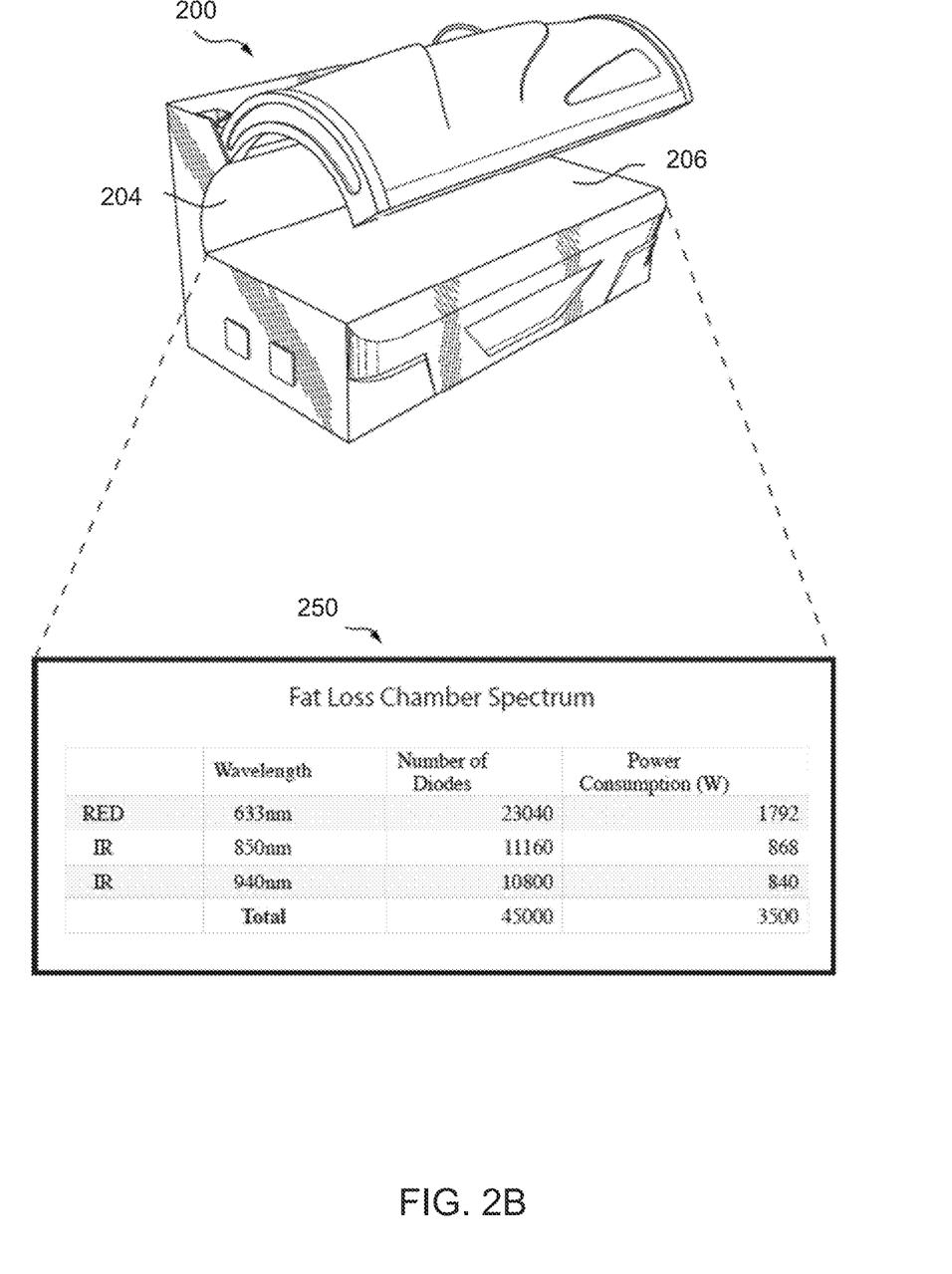
FIG. 2b illustrates a light therapy chamber with operating parameters in accordance with an example.

In another example, as illustrated in FIG. 2b, a light therapy device 200 with a combination of light sources 204, 206 can be configured to include (a) a first discrete light source that can emit at a wavelength of about 633 nm, (b) a second discrete light source that can emit at a wavelength of about 850 nm, and (c) a third discrete light source that can emit at a wavelength of about 940 nm. The table 250 in FIG. 2B depicts a fat loss chamber spectrum using 3 wavelengths of light.

In this example, (a) about 23040 first discrete light sources can emit at a wavelength of about 633 nm, (b) about 11160 second discrete light sources can emit at a wavelength of about 850 nm, and (c) about 10800 third discrete light sources can emit at a wavelength of about 940 nm.

In this example, the total power consumption in Watts (W) can be 3500. In this example, (a) the first discrete light sources can consume about 1792 W, (b) the second discrete light sources can consume about 868 W, and (c) the third discrete light sources can consume about 840 W.

Figure 3A:
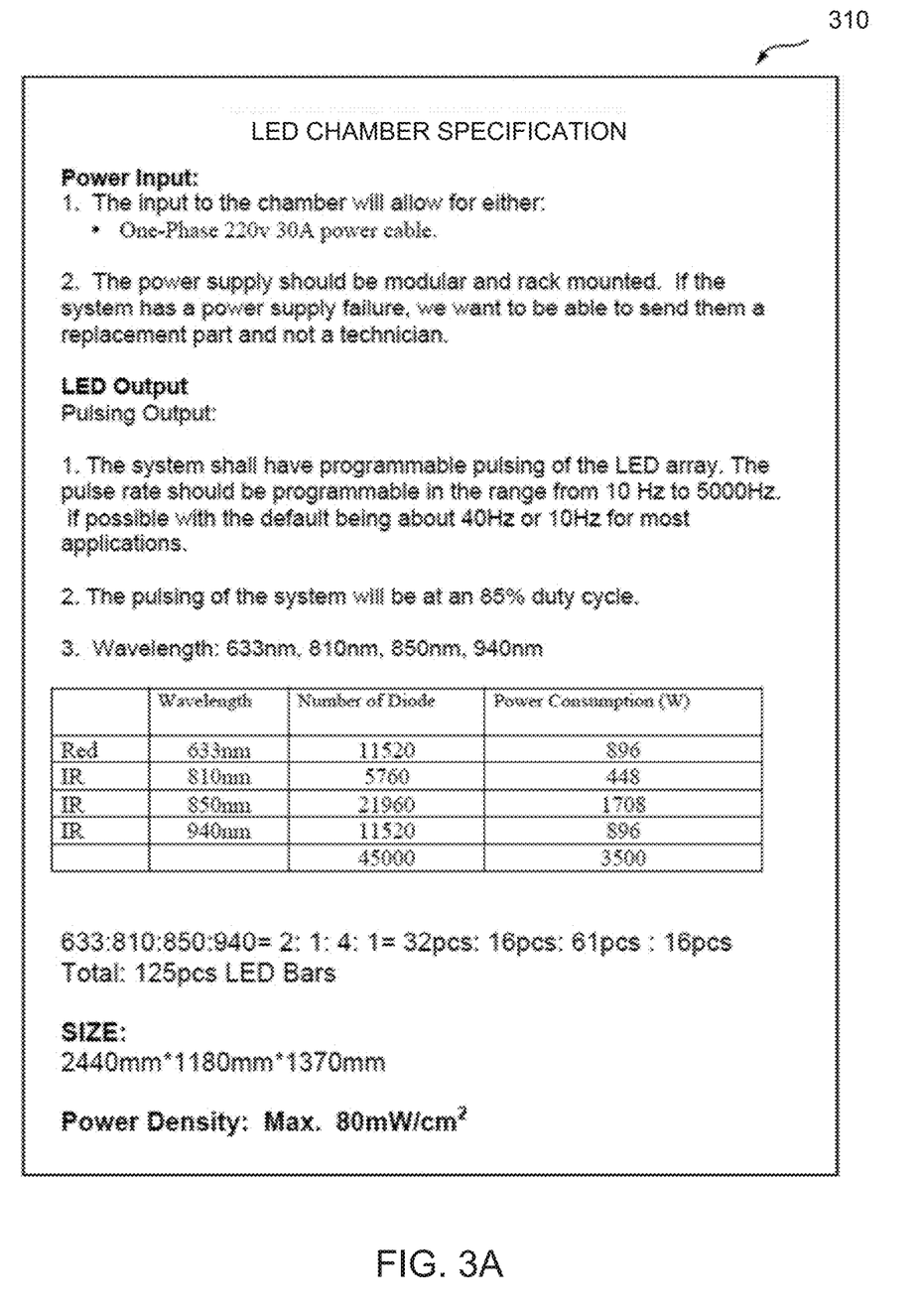
FIG. 3a depicts specifications for a light therapy chamber including 4 wavelengths of light in accordance with an example.

In another example, as depicted in FIG. 3a, a specification 310 provides for a power input and power supply. In this example a synergistic combination of 4 discrete wavelengths of light (e.g., 633 nm, 810 nm, 850 nm, and 940 nm) can provide varying penetrations into the tissue of a subject. For example, a light source radiating at a wavelength of about 633 nm can penetrate about 1-2 millimeters (mm) through the epidermis into the hypodermis. Light source radiating at a wavelength of about 810 nm, or about 850 nm, or about 940 nm can penetrate at least 2-3 mm through the epidermis into the hypodermis.

Figure 3B:
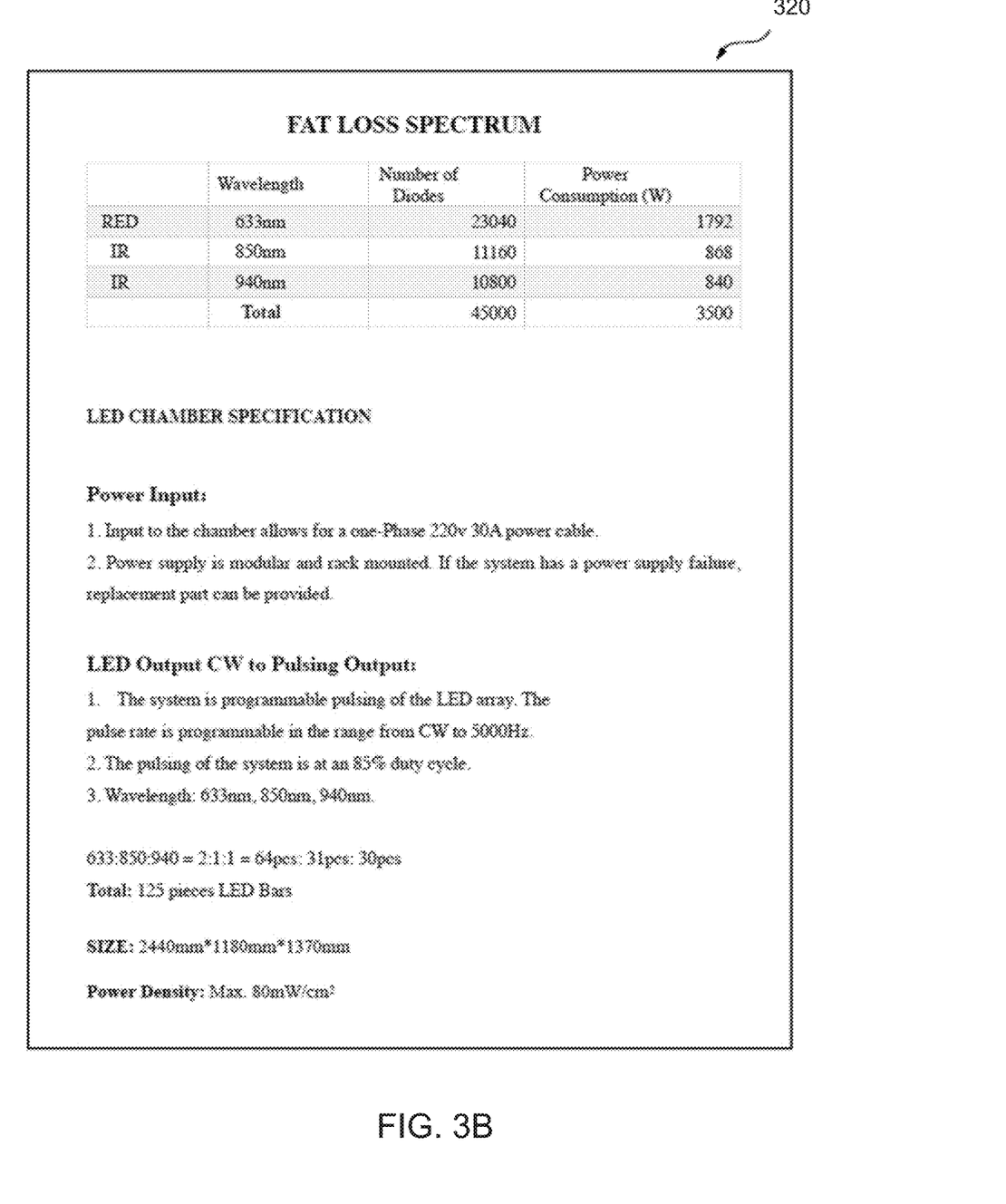
FIG. 3b depicts specifications for a light therapy chamber including 3 wavelengths of light in accordance with an example.

In another example, as depicted in FIG. 3b, a specification 320 provides for a power input, power supply, LED output, a continuous wave configuration, a pulsing configuration, a power density, and a size. In this example a synergistic combination of 3 discrete wavelengths of light (e.g., 633 nm, 850 nm, and 940 nm) can provide varying penetrations into the tissue of a subject. For example, a light source radiating at a wavelength of about 633 nm can penetrate about 1-2 millimeters (mm) through the epidermis into the hypodermis. Light source radiating at a wavelength of about 850 nm or about 940 nm can penetrate at least 2-3 mm through the epidermis into the hypodermis.

The light therapy device can comprise a combination of light sources including one or more of: a light-emitting diode (LED), a laser, a sodium lamp, a gas discharge lamp, a metal vapor lamp, or combinations thereof.

Figure 4:
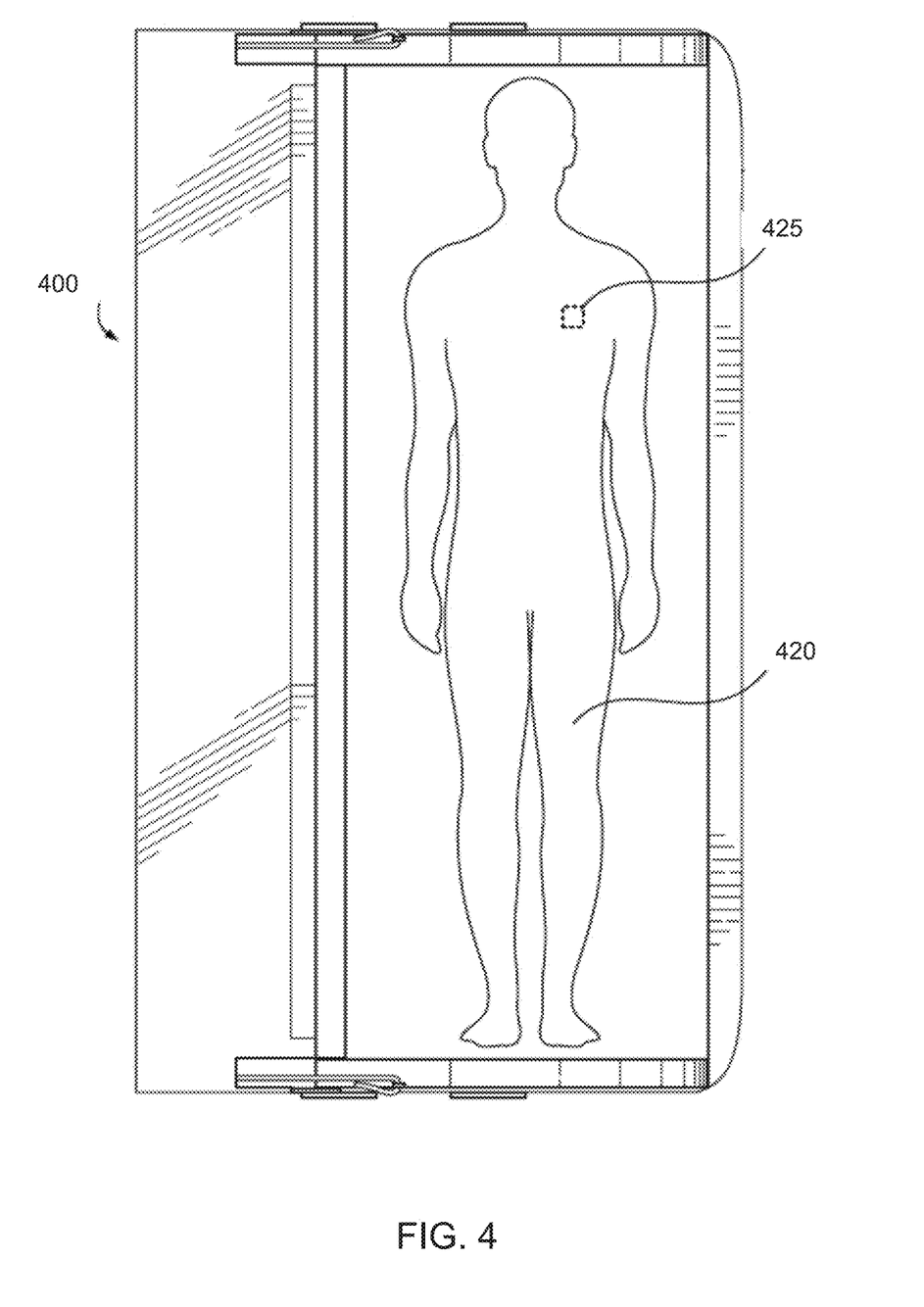
FIG. 4 illustrates a light therapy chamber depicting energy emission per surface area on the body of a subject in accordance with an example.

In another example, as illustrated in FIG. 4, a subject 420 can be positioned in a light therapy device 400. The light therapy device 400 can include a combination of light sources configured to radiate a combined power density limited to be between about 5 milliwatts (mW)/centimeters squared (cm2) to about 250 mW/cm2. In another example, the combined power density of the combination of light sources can be limited to be between about 25 mW/cm$^2$ to about 150 mW/cm$^2$. In another example, the combined power density of the combination of light sources can be limited to be between about 40 mW/cm$^2$ to about 120 mW/cm$^2$. In another example, the combined power density of the combination of light sources can be limited to be between about 60 mW/cm$^2$ to about 100 mW/cm$^2$.

In another example, the light therapy device 400 can be configured to radiate a selected combined power on a portion 425 of a subject 420. The light therapy device 400 can include a combination of light sources configured to radiate a combined power limited to be between about 5 Joules(J)/centimeters squared (cm2) to about 500 J/cm$^2$ based on a time period of about 10 minutes. In another example, the combined power of the combination of light sources can be limited to be between about 20 J/cm$^2$ to about 300 J/cm$^2$. In another example, the combined power of the combination of light sources can be limited to be between about 20 J/cm$^2$ to about 200 J/cm$^2$. In another example, the combined power of the combination of light sources can be limited to be between about 20 J/m$^2$ to about 100 J/cm$^2$.

In another example, the light therapy device 400 can comprise a combination of light sources. The combination of light sources can be configured in one or more of: a flat configuration, an arcuate configuration, a 180-degree arc configuration, a 360-degree arc configuration, or a combination thereof. In another example, the housing of the light therapy device can comprise one or more of a bed, a booth, a panel, or a tube.

The combination of light sources can vary in density across the light therapy device. For example, a light therapy device can include additional light sources around the head in order to allow for deeper penetration into the skull of the subject. In another example, the combination of light sources can have a density that is substantially uniform across the light therapy device.

In another example, the combination of light sources can be selected to provide a holistic benefit to the subject. When the subject cannot maintain homeostasis, and wherein if the disease is not ameliorated then the subject's health continues to deteriorate. The holistic benefit to the subject can restore homeostasis to the subject.

The light therapy device can further comprise a control panel or graphical user interface (GUI). The light therapy device can further comprise one or more speakers.

In another example, a light therapy system can comprise a light therapy device and a controller configured to select a parameter of emission by the light sources. The controller can be configured to adjust a pulse rate of the combination of light sources from about 10 hertz (Hz) to about 5 kilohertz (kHz). The controller can be further configured to adjust a combined power density of the combination of light sources from about 5 milliwatts (mW)/centimeters squared (cm$^2$) to about 250 mW/cm$^2$. The controller can be further configured to adjust a combined power of the combination of light sources from about 5 Joules/centimeters squared (cm$^2$) to about 500 Joules/cm$^2$ based on a time period of about 10 minutes.

In another example, the controller can be further configured to adjust a timer to activate or deactivate the power of the light therapy device. In another example, the controller can be further configured to adjust a combined power density of the combination of light sources over a selected period of time. In another example, the controller can be further configured to adjust a combined power of the combination of light sources over a selected period of time. In another example, the controller can be further configured to adjust an output of one or more speakers electrically coupled to the light therapy can further comprise a graphical user interface electrically coupled to the light therapy device and one or more speakers electrically coupled to the light therapy device.

Figure 5:
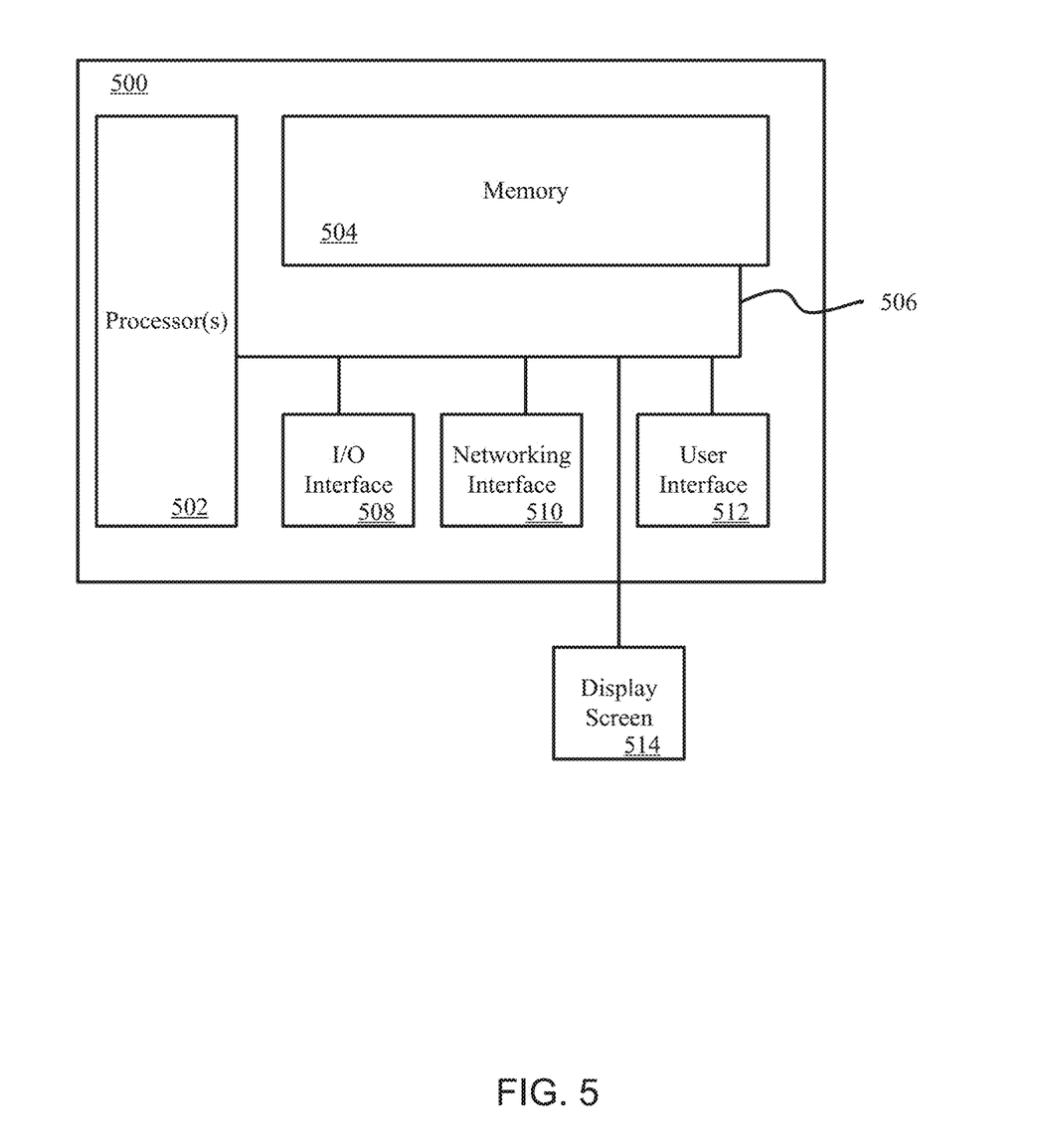
FIG. 5 illustrates a general computing system or device in accordance with an example.

FIG. 5 illustrates a general computing system or device 500 that can be employed in the present technology. The computing system 500 can include a processor 502 in communication with a memory 504. The memory 504 can include any device, combination of devices, circuitry, and the like that is capable of storing, accessing, organizing, and/or retrieving data. Non-limiting examples include SANs (Storage Area Network), cloud storage networks, volatile or non-volatile RAM, phase change memory, optical media, hard-drive type media, and the like, including combinations thereof.

The computing system or device 500 additionally includes a local communication interface 506 for connectivity between the various components of the system. For example, the local communication interface 506 can be a local data bus and/or any related address or control busses as may be desired.

The computing system or device 500 can also include an I/O (input/output) interface 508 for controlling the I/O functions of the system, as well as for I/O connectivity to devices outside of the computing system 500. A network interface 510 can also be included for network connectivity. The network interface 510 can control network communications both within the system and outside of the system. The network interface can include a wired interface, a wireless interface, a Bluetooth interface, optical interface, and the like, including appropriate combinations thereof. Furthermore, the computing system 500 can additionally include a user interface 512, a display device 514, as well as various other components that would be beneficial for such a system.

The processor 502 can be a single or multiple processors, and the memory 504 can be a single or multiple memories. The local communication interface 506 can be used as a pathway to facilitate communication between any of a single processor, multiple processors, a single memory, multiple memories, the various interfaces, and the like, in any useful combination.

Figure 6:
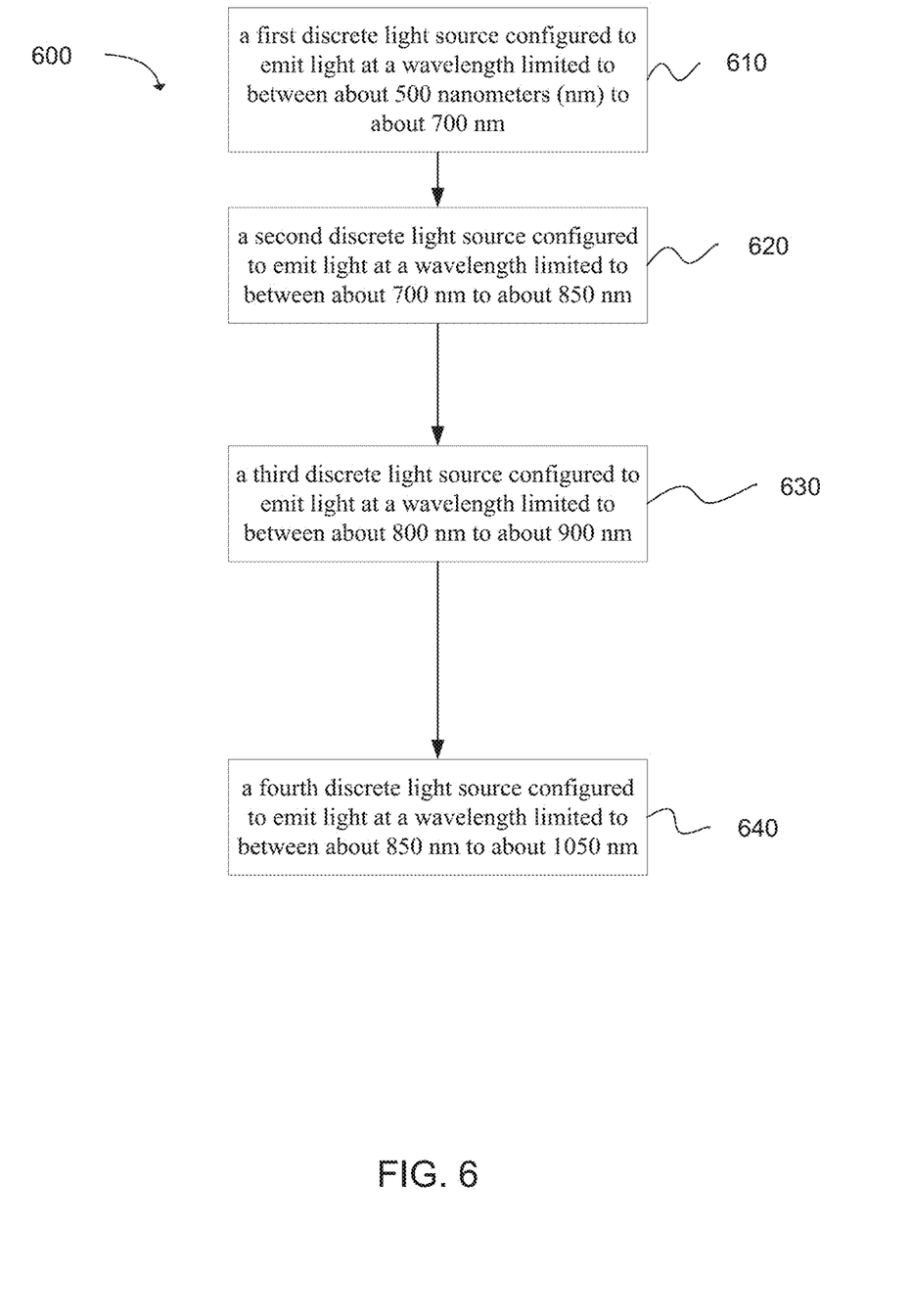
FIG. 6 depicts functionality of a light therapy device in accordance with an example.

Another example provides functionality 600 of a light therapy device, as shown in the flow chart in FIG. 6. The light therapy device can comprise a housing and a combination of light sources coupled to the housing in an orientation operable to radiate a subject. The combination of light sources can comprise a first discrete light source configured to emit light at a wavelength limited to between about 500 nanometers (nm) to about 700 nm, as in block 610. The combination of light sources can comprise a second discrete light source configured to emit light at a wavelength limited to between about 700 nm to about 850 nm, as in block 620. The combination of light sources can comprise a third discrete light source configured to emit light at a wavelength limited to between about 800 nm to about 900 nm, as in block 630. The combination of light sources can comprise a fourth discrete light source configured to emit light at a wavelength limited to between about 850 nm to about 1050 nm, as in block 640.

Figure 7:
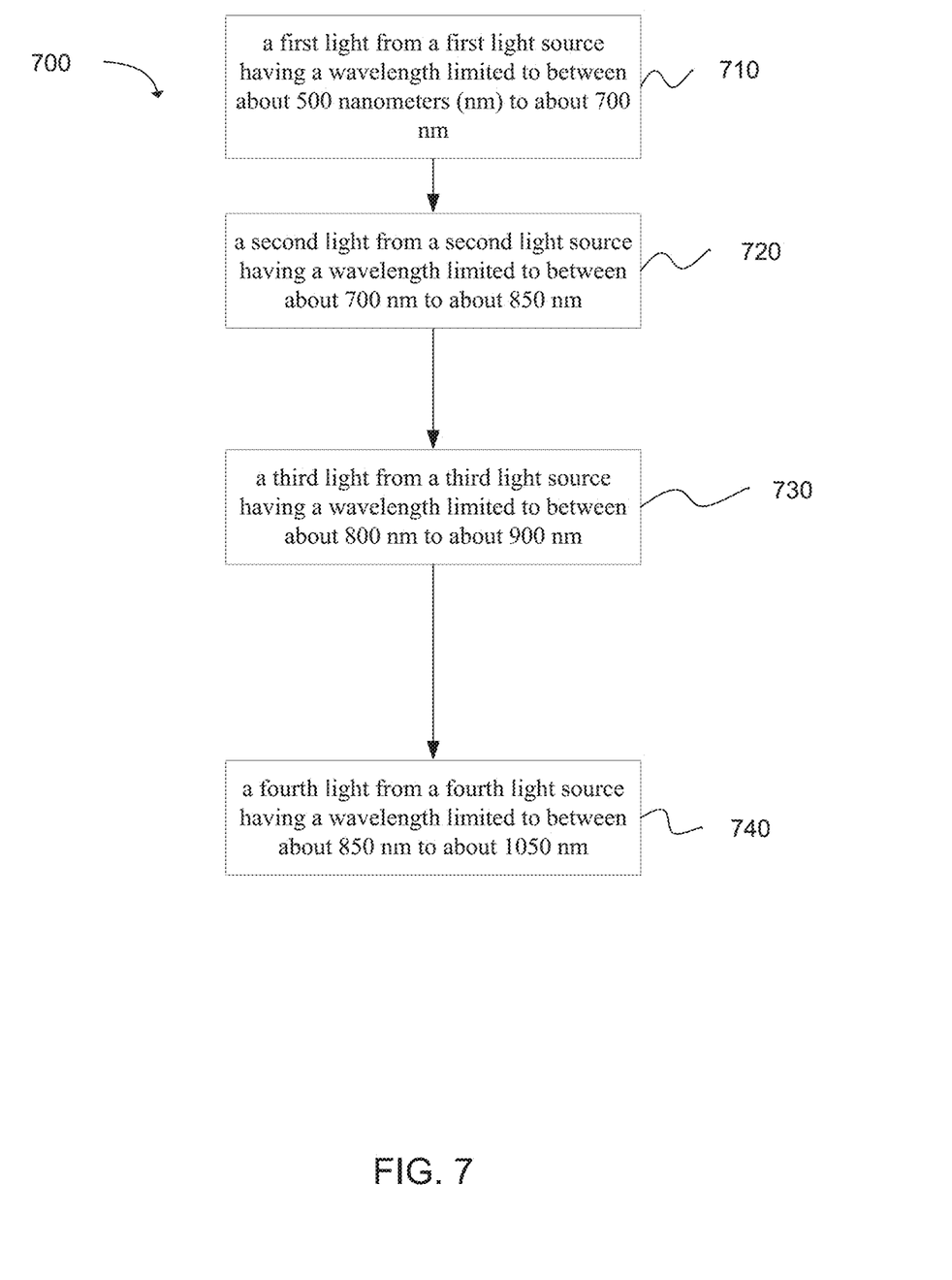
FIG. 7 depicts a method of treating a subject with a condition that is responsive to light therapy in accordance with an example.

Another example provides a method 700 of treating a subject with a condition that is responsive to light therapy, as shown in the flow chart in FIG. 7. The method can comprise irradiating the subject with a therapeutically effective combination. The therapeutically effective combination can include a first light from a first light source having a wavelength limited to between about 500 nanometers (nm) to about 700 nm, as in block 710. The therapeutically effective combination can include a second light from a second light source having a wavelength limited to between about 700 nm to about 850 nm, as in block 720. The therapeutically effective combination can include a third light from a third light source having a wavelength limited to between about 800 nm to about 900 nm, as in block 730. The therapeutically effective combination can include a fourth light from a fourth light source having a wavelength limited to between about 850 nm to about 1050 nm, as in block 740.

Figure 8:
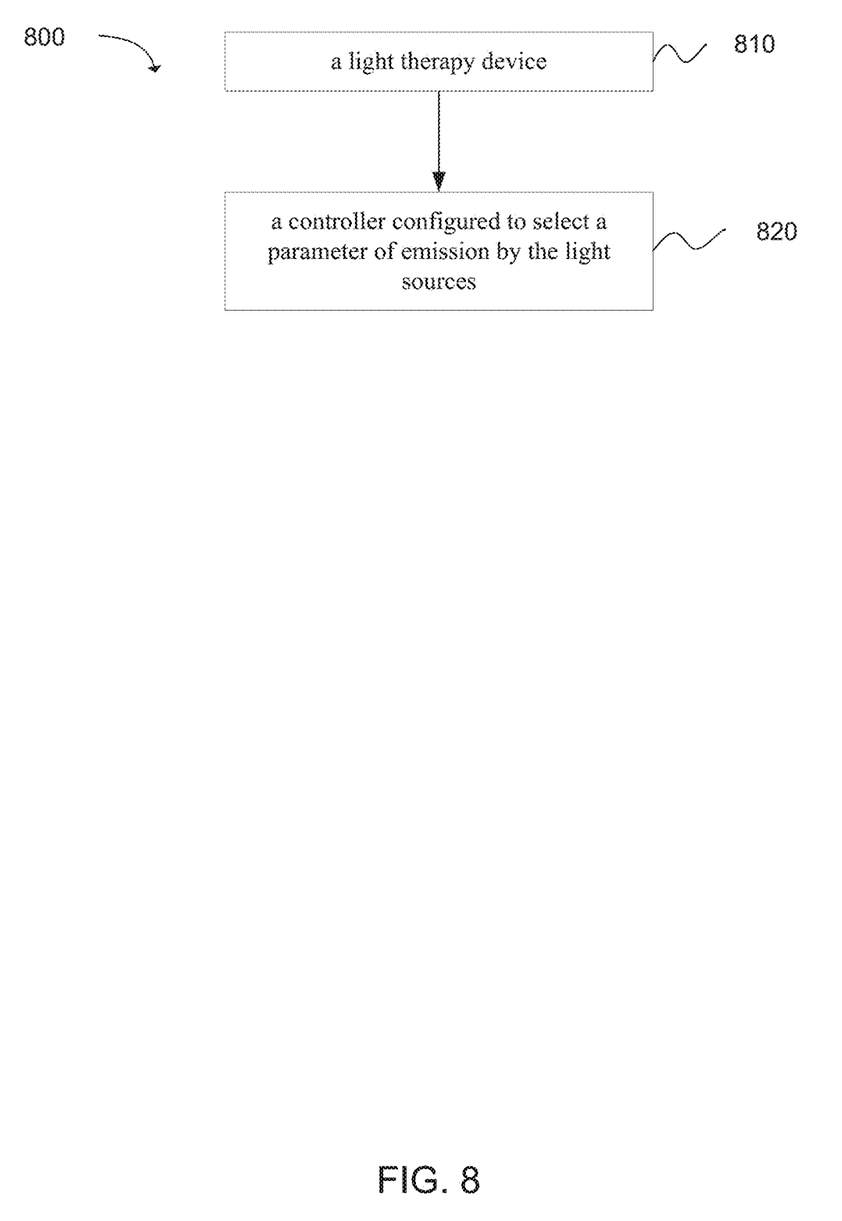
FIG. 8 depicts a functionality of a light therapy system in accordance with an example.

Another example depicts a light therapy system, as shown in the flow chart in FIG. 8. The system can comprise a light therapy device, as in block 810. The system can further comprise a controller configured to select a parameter of emission by the light sources, as in block 820.

Various techniques, or certain aspects or portions thereof, can take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. Circuitry can include hardware, firmware, program code, executable code, computer instructions, and/or software. A non-transitory computer readable storage medium can be a computer readable storage medium that does not include signal. In the case of program code execution on programmable computers, the computing device can include a processor, a storage medium readable by the processor (including volatile and non-volatile memory and/or storage elements), at least one input device, and at least one output device. The volatile and non-volatile memory and/or storage elements can be a RAM, EPROM, flash drive, optical drive, magnetic hard drive, solid state drive, or other medium for storing electronic data. The node and wireless device can also include a transceiver module, a counter module, a processing module, and/or a clock module or timer module. One or more programs that can implement or utilize the various techniques described herein can use an application programming interface (API), reusable controls, and the like. Such programs can be implemented in a high level procedural or object oriented programming language to communicate with a computer system. However, the program(s) can be implemented in assembly or machine language, if desired. In any case, the language can be a compiled or interpreted language, and combined with hardware implementations. Exemplary systems or devices can include without limitation, laptop computers, tablet computers, desktop computers, smart phones, computer terminals and servers, storage databases, and other electronics which utilize circuitry and programmable memory, such as household appliances, smart televisions, digital video disc (DVD) players, heating, ventilating, and air conditioning (HVAC) controllers, light switches, and the like.

Methods

The present invention provides a method of treating a subject with light therapy. The present method can be used to treat, prevent, or reduce the incidence of any disease, disorder, or condition where light therapy is beneficial. Exemplary diseases, disorders, or conditions, include but are not limited to, infections, inflammatory diseases, pain (e.g., muscle or joint), stiffness (e.g., joint or muscle), arthritis, obesity, and the like.

In one embodiment, the method comprises the treatment, prevention, or reduction of incidence of an infection in a subject, including infections caused by a virus, a fungus, a protozoan, a parasite, an arthropod or a bacterium, including a bacterium that has developed resistance to one or more antibiotics. In some embodiments, the infection is caused by a bacterium. In one embodiment, the bacterium is *Acetobacter baumanii*. In another embodiment, the bacterium is Methicillin-resistant *Staphylococcus aureus*. In another embodiment, the bacterium is *Escherichia coli*. In other embodiments, the infection is caused by a virus. In one embodiment, the virus is Influenza H1N1. In other embodiments, the infection is caused by a fungus. In one embodiment, the fungus is *Trichophyton Rubrum*.

In one embodiment, the present invention provides a method of treating skin inflammation, including inflammation associated with psoriasis, dermatitis (atopic, contact, sebborheic, etc), eczema, tinea pedis, and rosacea. In one embodiment, the present invention provides a method of treating pain including: pain in limbs, joint pain, muscle pain, neuropathy, shingles, poor circulation, the like, or combinations thereof. In another embodiment, the present invention provides a method of treating one or more of rheumatoid arthritis, osteoarthritis, psoriatic arthritis, fibromyalgia, chronic fatigue, the like, or combinations thereof.

In another example, the present invention provides a method of treating one or more of: alcohol or drug poisoning, intoxication, alcohol "hang over," toxicity induced by cytotoxic chemotherapy, radiation trauma, AIDS-associated cachexia, HIV Aids, shingles, frostbite, heavy metal poisoning, burns including laser burn, sun burn, traumatic burn, thermal burn, chemical burn, acne, pressure sore, autism, scar tissue, Parkinson's disease, hepatitis B. hepatitis C, upper respiratory virus infections (cold), cystic fibrosis, acne, insect bites (mosquito, spider, etc), pain in limbs, neuropathy, Reflex Sympathetic Dystrophy (RSD), rheumatoid arthritis, multiple sclerosis, osteoarthritis, psoriasis, psoriatic arthritis, jet lag, kidney disease (CRF, CKD), and akathisia, tardive dyskinesia, obesity, decreased immunity, inflammation (including muscle tissue, joint, bone, connective tissue, epithelial tissue, or smooth muscle tissue inflammation among others), angina, heart disease, and cardiac reperfusion injury, lung-and-neurological-diseases such as acute respiratory-disease, emphysema, pulmonary fibrosis and associated muscle wasting, asthma, migraine headaches, Parkinson's-disease, herpes zoster, HSV, hepatitis B&C, and influenza, fibromyalgia, osteoporosis/osteomalacia, cancer including but not limited to brain, head and neck, thyroid, lung, esophagus, stomach, intestine, liver, pancreas, kidney uterine, ovarian, prostate, leukemia (acute and chronic), lymphoma, multiple myeloma, and others, systemic sclerosis (scleroderma) syndrome, sepsis, trauma, wrinkles, sagging skin, atopic dermatitis and eczema, athletic overtraining and muscle fatigue; schizophrenia, bipolar disorder, major depressive disorder, dementia, autism, Attention Deficit Hyperactive Disorder (ADHD); overdose of acetaminophen, low energy, drug toxicity, eye problems including cataracts, glaucoma, macular degeneration, macular dystrophy, diabetic retinopathy, decreased visual acuity, diabetic retinopathy, and contrast sensitivity; biomolecule imbalances resulting from traumatic head injury or other causes, or infertility in men and women.

The present invention includes a therapeutically effective combination that can stimulate one or more of: blood circulation, lactic acid clearance, tissue regeneration, muscle mobility, joint mobility, muscle regeneration, weight loss, or combinations thereof.

In certain embodiments, a subject can be irradiated with a therapeutically effective combination. The therapeutically effective combination can be radiated once an hour, once a day, once a week, once every two weeks, once a month, once every two months, once a year, and any and all ranges therebetween as required to treat the subject. In one embodiment, the therapeutically effective combination can be radiated once a week. In another embodiment, the therapeutically effective combination can be radiated once a week for four consecutive weeks.

In certain embodiments, the duration of irradiating the subject can be varied in order to optimize delivery. In one embodiment, the therapeutically effective combination is administered to the subject over a time period of less than 10 minutes. In another embodiment, the therapeutically effective combination is administered to the subject over a time period of about 10 minutes. In another embodiment, the therapeutically effective combination is administered to the subject over a time period of about 20 minutes. In another embodiment, the therapeutically effective combination is administered to the subject over a time period of about 30 minutes. In another embodiment, the therapeutically effective combination is administered to the subject over a time period of about 60 minutes. In another embodiment, the therapeutically effective combination is administered to the subject over a time period of about 90 minutes. In another embodiment, the therapeutically effective combination is administered to the subject over a time period of about 120 minutes.

In another embodiment, the therapeutically effective combination can be configured to radiate a combined power density limited to between about 5 milliwatts (mW)/centimeters squared (cm2) to about 250 mW/cm$^2$. In another embodiment, the therapeutically effective combination can be configured to radiate a combined power limited to between about 5 Joules/centimeters squared (cm$^2$) to about 500 Joules/cm$^2$ based on a time period of about 10 minutes.

In another embodiment, the therapeutically effective combination can include: a plurality of first light sources present from about 20% to about 30% of the therapeutically effective combination; a plurality of second light sources present from about 8% to about 16% of the therapeutically effective combination; a plurality of third light sources present from about 40% to about 60% of the therapeutically effective combination; and a plurality of second light sources present from about 15% to about 35% of the therapeutically effective combination.

In another embodiment, the therapeutically effective combination can be irradiated on a target site of a subject, wherein the target site can include a portion of one or more of: a head, an arm, a leg, a torso, a neck, a heart, blood, blood vessels, arteries, veins, a mouth, an esophagus, a stomach, a small intestine, a large intestine, a rectum, and an anus, a liver, a pancreas, lymph nodes, a spleen, bone marrow, a thymus, a brain, a spinal cord, skeletal muscle, smooth muscle, cardiac muscle, a penis, a testes, a vagina, a uterus, ovaries, a bone, a tendon, a ligament, cartilage, teeth, a trachea, a diaphragm, lungs, a kidney, a ureter, a bladder, a sphincter muscle, a urethra, skin, hair, nails, and the like. In another embodiment, the therapeutically effective combination can be irradiated on about a full body of a subject.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

A 45 year-old male subject with arthritis in the left knee, chronic pain in the right arm, a sore left arm after an athletic injury, stiffness in the back, and inflammation in the chest—is positioned in a 360-degree full body light therapy device. The 360-degree light therapy device is configured as follows: (a) a first type of light emitting diode (LED) emits a wavelength of 633 nm, (b) a second type of LED emits a wavelength of 810 nm, (c) a third type of LED emits a wavelength of about 850 nm, and (d) a fourth type of LED emits a wavelength of about 940 nm.

The light therapy device has: 11520 first LED types (about 25.6% of the total LEDs), 5760 second LED types (about 12.8% of the total LEDs), 21960 third LED types (about 48.8% of the total LEDs), and 11520 fourth LED types (about 25.6% of the total LEDs). The power consumption of the first LED types is about 896 W. The power consumption of the second LED types is about 448 W. The power consumption of the third LED types is about 1708 W. The power consumption of the fourth LED types is about 896 W. The LEDs emit with a power density of about 80 mW/cm$^2$. The LEDs emit power at about 50 Joules/cm$^2$ in a time period of about 10 minutes. The light therapy device is configured to pulse at a rate of about 40 hertz with an 85% duty cycle.

The subject undergoes a 30-minute session of irradiation once per week for 4 straight weeks. After the 4 weeks of treatment, the subject's left knee arthritis mitigates by about 33%, the subject's chronic pain in the right arm reduces by 50%, the subject's soar left arm mitigates about 80%, the subject's stiffness in the back reduces by about 20%, and the subject's inflammation in the chest reduces by 90%.

Example 2

A 30 year-old female subject with muscle pain in the left leg and joint pain in near the left ankle—is positioned in a 360-degree full body light therapy device. The 360-degree light therapy device is configured as follows: (a) a first type of light emitting diode (LED) emits a wavelength of 550 nm, (b) a second type of LED emits a wavelength of 750 nm, (c) a third type of LED emits a wavelength of about 850 nm, and (d) a fourth type of LED emits a wavelength of about 900 nm.

The light therapy device has: 11520 first LED types (about 25.6% of the total LEDs), 5760 second LED types (about 12.8% of the total LEDs), 21960 third LED types (about 48.8% of the total LEDs), and 11520 fourth LED types (about 25.6% of the total LEDs). The LEDs emit with a power density of about 80 mW/cm$^2$. The LEDs emit power at about 50 Joules/cm$^2$ in a time period of about 10 minutes. The light therapy device is configured to pulse at a rate of about 10 hertz with an 85% duty cycle.

The subject undergoes a 30-minute session of irradiation twice a month for 3 straight months. After the 3 months of treatment, the subject's muscle pain in the left leg mitigates by about 80%, and the subject's joint pain near the left ankle reduces by about 50%.

Example 3

A 20 year-old overweight male subject with poor blood circulation, excess lactic acid, weak arms, weak joint and muscle mobility, and—is positioned in a 360-degree full body light therapy device. The 360-degree light therapy device is configured as follows: (a) a first type of light emitting diode (LED) emits a wavelength of 650 nm, (b) a second type of LED emits a wavelength of 800 nm, (c) a third type of LED emits a wavelength of about 835 nm, and (d) a fourth type of LED emits a wavelength of about 1000 nm.

The light therapy device has: 11520 first LED types (about 25.6% of the total LEDs), 5760 second LED types (about 12.8% of the total LEDs), 21960 third LED types (about 48.8% of the total LEDs), and 11520 fourth LED types (about 25.6% of the total LEDs). The LEDs emit with a power density of about 80 mW/cm$^2$. The LEDs emit power at about 50 Joules/cm$^2$ in a time period of about 10 minutes. The light therapy device is configured to pulse at a rate of about 5 kHz with an 85% duty cycle.

The subject undergoes a 30-minute session of irradiation once per week 8 straight weeks. After the 8 weeks of treatment, the subject loses 3% of previous body weight, increases weight-lifting ability by about 10% in the arms, and increases mobility by about 5%.

Example 4

A 50 year-old female subject with pain in the left wrist and a headache—is positioned in a 360-degree full body light therapy device. The 360-degree light therapy device is configured as follows: (a) a first type of light emitting diode (LED) emits a wavelength of 633 nm, (b) a second type of LED emits a wavelength of 810 nm, (c) a third type of LED emits a wavelength of about 850 nm, and (d) a fourth type of LED emits a wavelength of about 960 nm. The light therapy device is adapted to cluster a higher density of LEDs near the head of the subject and the left wrist of the subject.

The light therapy device has: 23% first LED types, 8% second LED types, 45% third LED types, and 26% fourth LED types. The LEDs emit with a power density of about 80 mW/cm$^2$. The LEDs emit power at about 50 Joules/cm$^2$ in a time period of about 10 minutes. The light therapy device is configured with a continuous wave.

The subject undergoes a 30-minute session of irradiation once per week for 2 straight weeks. After the 2 weeks of treatment, the subject's left wrist pain reduces by 90% and the subject's headache is gone.

What is claimed is:

1. has been amended to:
A light therapy device, comprising: a housing: and a combination of light sources including a red-light source, first and second near-infrared light sources, and an infrared light source having an orientation in the housing that provides light therapy, wherein the combination of light sources is operable to radiate a combined power density limited to be between about 25 milliwatts (mW)/centimeters (cm$^2$) to about 250 mW/cm$^2$, wherein the red-light source is operable to emit light at a wavelength limited to be between about 600 nanometers (nm) to about 665 nm, wherein the first near-infrared light source is operable to emit light at a wavelength limited to be between about 800 nm to about 830 nm; wherein the second near-infrared light source is operable to emit light at a wavelength limited to be between about 820 nm to about 880 nm; and wherein the infrared light source is operable to emit light at a wavelength limited to be between about 900 nm to about 1000 nm; wherein the combination of light sources includes red-light sources limited to between about 20% to about 30% of the combination of light sources, and first and second near-infrared light sources limited to between about 48% to about 65% of the combination of light sources, and infrared light sources limited to between about 15% to about 32% of the combination of light sources, wherein the total percentage of the red-light sources, near-infrared light sources, and infrared light sources is no greater than 100% of the combination of light sources.

2. The light therapy device of claim 1, wherein the combination of light sources is operable to radiate a combined power density limited to between about 60 milliwatts mW/cm² to about 250 mW/cm².

3. The light therapy device of claim 1, wherein the combination of light sources is operable to radiate a combined power limited to between about 20 Joules/centimeters squared (cm²) to about 500 Joules/cm² in a time period of about 10 minutes.

4. The light therapy device of claim 1, wherein the combination of light sources is configured in one or more of: a flat configuration, an arcuate configuration, a 180-degree arc configuration, a 360-degree arc configuration, or a combination thereof.

5. The light therapy device of claim 1, wherein the housing comprises one or more of a bed, a booth, a panel, or a tube.

6. The light therapy device of claim 1, wherein the combination of light sources comprises one or more of: a light-emitting diode (LED), a laser, a sodium lamp, a gas discharge lamp, a metal vapor lamp, or combinations thereof.

7. The light therapy device of claim 1, wherein the combination of light sources is configured to pulse at a rate limited to between about 10 hertz (Hz) to about 5 kilohertz (kHz) using a duty cycle limited to between about 75% to about 100%.

8. The light therapy device of claim 1, wherein the combination of light sources comprises at least about 45,000 light sources.

9. A light therapy system, comprising:
a light therapy device as recited in claim 1; and
a controller configured to select a parameter of emission by the light sources.

10. The light therapy system of claim 9, wherein the controller is further configured to adjust a pulse rate of the combination of light sources from about 10 hertz (Hz) to about 5 kilohertz (kHz).

11. The light therapy system of claim 9, wherein the controller is further configured to:
adjust a combined power density of the combination of light sources from about 60 mW/cm² to about 250 mW/cm²; or adjust a combined power of the combination of light sources from about 20 Joules/centimeters squared (cm²) to about 500 Joules/cm² based on a time period of about 10 minutes.

12. The light therapy system of claim 9, wherein the controller is further configured to:
adjust a timer to activate or deactivate the power of the light therapy device; or
adjust a combined power density of the combination of light sources over a selected period of time; or
adjust a combined power of the combination of light sources over a selected period of time; or
adjust an output of one or more speakers electrically coupled to the light therapy device.

13. The light therapy system of claim 9, further comprising:
a graphical user interface electrically coupled to the light therapy device; and
one or more speakers electrically coupled to the light therapy device.

14. The light therapy device of claim 1, wherein the combined power density is limited to be about 25 mW/cm² to about 150 mW/cm².

15. The light therapy device of claim 1, wherein the housing comprises is a bed.

16. has been amended to:
A method of treating a subject with a condition that is responsive to light therapy comprising: irradiating the subject with a therapeutically effective combination of a combination of light sources including a red-light source, first and second near-infrared light sources, and an infrared light source that provides light therapy, wherein the combination of light sources 3 is operable to radiate a combined power density limited to be between about 25 milliwatts (mW)/centimeters (cm²) to about 250 mW/cm²,wherein the red-light source is operable to emit light at a wavelength limited to be between about 600 nanometers (nm) to about 665 nm, wherein the first near-infrared light source is operable to emit light at a wavelength limited to be between about 800 nm to about 830 nm, wherein the second near-infrared light source is operable to emit light at a wavelength limited to be between about 820 nm to about 880 nm, and wherein the infrared light source is operable to emit light at a wavelength limited to be between about 900 nm to about 1000 nm; wherein the therapeutically effective combination includes a total number of light sources including red-light sources limited to between about 20% to about 30% of the combination of light sources, and first and second near-infrared light sources limited to between about 48% to about 65% of the combination of light sources, and infrared light sources limited to between about 15% to about 32% of the combination of light sources, wherein the total percentage of the red-light sources, near-infrared light sources, and infrared light sources is no greater than 100% of the combination of light sources.

17. The method of claim 16, wherein the therapeutically effective combination treats one or more of: pain, stiffness, inflammation, muscle pain, joint pain, arthritis, obesity, blood circulation, lactic acid clearance, tissue regeneration, muscle mobility, joint mobility, muscle regeneration, weight loss, or combinations thereof.

18. The method of claim 16, wherein the therapeutically effective combination is configured to radiate a combined power density limited to between about 60 mW/cm² to about 250 mW/cm².

19. The method of claim 16, wherein the therapeutically effective combination is configured to radiate a combined power limited to between about 20 Joules/centimeters squared (cm²) to about 500 Joules/cm² in a time period of about 10 minutes.

20. The method of claim 16, wherein a region or full body of a subject is irradiated.

21. The method of claim 16, wherein a full body of a subject is irradiated simultaneously.

* * * * *